(12) United States Patent
Murakami et al.

(10) Patent No.: US 10,131,076 B2
(45) Date of Patent: Nov. 20, 2018

(54) BULK-DENSITY MEASURING DEVICE FOR PRE-EXPANDED PARTICLES AND METHOD FOR MANUFACTURING PRE-EXPANDED PARTICLES

(71) Applicant: Kaneka Corporation, Osaka (JP)

(72) Inventors: Kyosuke Murakami, Osaka (JP); Shinobu Ochikoshi, Osaka (JP); Toru Yoshida, Osaka (JP)

(73) Assignee: KANEKA CORPORATION, Osaka (JP)

( * ) Notice: Subject to any disclaimer, the term of this patent is extended or adjusted under 35 U.S.C. 154(b) by 225 days.

(21) Appl. No.: 15/029,784

(22) PCT Filed: Apr. 7, 2014

(86) PCT No.: PCT/JP2014/060111
§ 371 (c)(1),
(2) Date: Apr. 15, 2016

(87) PCT Pub. No.: WO2015/056461
PCT Pub. Date: Apr. 23, 2015

(65) Prior Publication Data
US 2016/0229096 A1    Aug. 11, 2016

(30) Foreign Application Priority Data

Oct. 18, 2013    (JP) .................................. 2013-217500

(51) Int. Cl.
*B29C 44/60*    (2006.01)
*B29C 44/34*    (2006.01)
(Continued)

(52) U.S. Cl.
CPC .......... *B29C 44/60* (2013.01); *B29C 44/3461* (2013.01); *C08J 9/16* (2013.01);
(Continued)

(58) Field of Classification Search
CPC ....... G01N 2009/022; G01N 2009/024; G01N 9/02; C08J 9/16; B29C 44/60; B29C 44/3461; B29K 2995/0063
(Continued)

(56) References Cited

U.S. PATENT DOCUMENTS

| 5,017,621 | A | * | 5/1991 | Shiiki | ...................... C08J 9/228 |
| | | | | | 264/DIG. 16 |
| 5,423,216 | A | * | 6/1995 | Kitamura | ................. G01N 9/02 |
| | | | | | 702/173 |
| 8,592,494 | B2 | * | 11/2013 | Matsumura | ........... C08F 255/02 |
| | | | | | 428/304.4 |

FOREIGN PATENT DOCUMENTS

| JP | S63-26549 A | 2/1988 |
| JP | H06-80816 A | 3/1994 |

(Continued)

OTHER PUBLICATIONS

International Search Report issued in PCT/JP2014/060111 dated Jul. 8, 2014 (2 pages).

*Primary Examiner* — Daniel S Larkin
(74) *Attorney, Agent, or Firm* — Osha Liang LLP (57) ABSTRACT

A bulk-density measuring device includes a first vessel in which contracted pre-expanded particles are swollen and recovered from contraction in a pressure-reduced state where a vessel internal pressure is lower than atmospheric pressure; a second vessel filled with the pre-expanded particles after being swollen in the first vessel in the pressure-reduced state where a vessel internal pressure is lower than the atmospheric pressure, and into which the pre-expanded particles of a constant volume are collected fractionally; a pressure-reducing unit that adjusts the vessel internal pressures of the first vessel and the second vessel to be lower (Continued)

than the atmospheric pressure; and a scale that measures a weight of the pre-expanded particles filled in the second vessel.

19 Claims, 4 Drawing Sheets

(51) Int. Cl.
    *C08J 9/16*           (2006.01)
    *G01N 9/02*         (2006.01)
    *B29K 23/00*        (2006.01)

(52) U.S. Cl.
    CPC ............ *G01N 9/02* (2013.01); *B29K 2023/06* (2013.01); *B29K 2023/12* (2013.01); *B29K 2995/0063* (2013.01); *C08J 2323/06* (2013.01); *G01N 2009/022* (2013.01); *G01N 2009/024* (2013.01)

(58) Field of Classification Search
    USPC .......................................................... 73/433
    See application file for complete search history.

(56) References Cited

FOREIGN PATENT DOCUMENTS

| | | |
|---|---|---|
| JP | 2006-096805 A | 4/2006 |
| JP | 2007-218588 A | 8/2007 |
| JP | 2009-161738 A | 7/2009 |
| JP | 2009-263639 A | 11/2009 |
| JP | 2010-209286 A | 9/2010 |
| WO | 2005/087475 A1 | 9/2005 |
| WO | 2011/086938 A1 | 7/2011 |

* cited by examiner

BULK-DENSITY MEASURING DEVICE FOR PRE-EXPANDED PARTICLES AND METHOD FOR MANUFACTURING PRE-EXPANDED PARTICLES

TECHNICAL FIELD

One or more embodiments of the present invention relate to a device for measuring bulk density of pre-expanded particles, in particular, second-stage expanded particles and a method for manufacturing the pre-expanded particles using the device. Polyolefin resin expanded particles are used as the pre-expanded particles.

BACKGROUND

An in-mold expanded molded product made of pre-expanded particles is provided by expanding resin particles (material particles) as a material using a pre-expanding device, a decompressing expansion device, or the like to manufacture pre-expanded particles having predetermined bulk density and filling a mold of an in-mold molding machine with the pre-expanded particles for in-mold expansion molding. The in-mold expanded molded product is used for diversified shapes and applications (cushioning materials, heat insulating materials, car interior members, core materials for car bumpers, cushioning packaging materials, returnable boxes, and the like).

In particular, as a method for manufacturing the pre-expanded particles having a high expansion ratio, a two-stage expansion method has been known in addition to a method for providing the pre-expanded particles having the high expansion ratio by the normal pre-expanding device, the normal decompressing expansion device, or the like. In the two-stage expansion method, pre-expanded particles having a low expansion ratio are once obtained, and then, the pre-expanded particles are further expanded using a second-stage expanding machine so as to obtain pre-expanded particles (second-stage expanded particles) having a higher expansion ratio.

In this case, it is important to make bulk density of the second-stage expanded particles constant. The constant bulk density enables an amount of the second-stage expanded particles that are supplied to a molding machine to be stable, thereby stabilizing quality of a molded product.

In general, as the method for manufacturing the second-stage expanded particles, for example, a batch-type method has been known. In the batch-type method, pre-expanded particles (first-stage expanded particles) to which an internal pressure of equal to or lower than 0.50 MPa has been previously applied are put into a second-stage expanding machine and are expanded to have predetermined bulk density with a heating medium such as steam. In this case, as a method for adjusting the bulk density of the second-stage expanded particles, the following method has been employed. That is, the second-stage expanded particles that have been second-stage expanded are collected, and the bulk density thereof is measured. Then, operating conditions (for example, internal pressure of the pre-expanded particles, heating steam pressure at the time of the second-stage expansion, and the like) of the second-stage expanding machine for a subsequent batch are required to be changed based on difference between the measured bulk density and a target value. The bulk density of the second-stage expanded particles is frequently adjusted by changing the operating conditions of the second-stage expanding machine in this manner in order to make the quality of the molded product stable.

As for the second-stage expanded particles having such low expansion ratio that volumes of the second-stage expanded particles themselves do not contract immediately after the second-stage expansion, a bulk-density measuring device for the second-stage expanded particles and a measuring method therefor have been disclosed (see, Patent Document 1 and Patent Document 2). With the bulk-density measuring device and the measuring method disclosed in them, the second-stage expanded particles are collected into a vessel of a constant volume (V) under atmospheric pressure and a weight (W) of the collected second-stage expanded particles is measured so as to calculate the bulk density (=W/V).

On the other hand, the following method for measuring the bulk density of the pre-expanded particles that are easy to contract in a dry process at the time of pre-expansion is also disclosed (see Patent Document 3). That is, the pre-expanded particles are held in a sample collection vessel for a constant period of time before the dry process, and then, are subjected to the dry process, so that contraction of the pre-expanded particles is suppressed to minimum. Then, the bulk density of the pre-expanded particles is measured.

The following bulk-density measuring method when contracted pre-expanded particles are made to recover from contraction has been known (see Patent Document 4 and Patent Document 5). That is, a weight w of the pre-expanded particles is measured, the total amount of the pre-expanded particles is put into a measuring cylinder, and pressure in the measuring cylinder is reduced so as to make them recover from the contraction. Then, a volume v of the pre-expanded particles is measured by reading a scale of the measuring cylinder, and the bulk density of w/v is measured.

CITATION LIST

Patent Literatures

Patent Document 1: JP-A No. H06-80816
Patent Document 2: International Publication WO 2005/087475
Patent Document 3: JP-A No. 2007-218588
Patent Document 4: International Publication WO 2011/086938
Patent Document 5: JP-A No. 2006-96805

The above-described conventionally well-known bulk-density measuring device for the second-stage expanded particles can stably measure the bulk density of the second-stage expanded particles with a low expansion ratio, which have the bulk density of equal to or higher than 30 g/L. On the other hand, when pre-expanded particles (for example, second-stage expanded particles) with a high expansion ratio, which have the bulk density of lower than 30 g/L, have been manufactured, the pre-expanded particles (second-stage expanded particles) immediately after the second-stage expansion contract and therefore the bulk density of the original pre-expanded particles (second-stage expanded particles) cannot be measured. For coping with this situation, the pre-expanded particles need to be dried for a long period of time to be recovered from the contraction, and then, the bulk density thereof is measured. Further, second-stage expansion conditions need to be changed based on difference between the measured bulk density and a target value, resulting in a problem.

In the current situation, the second-stage expanded particles are manufactured while production conditions are determined based on experiences of visual observations in the past.

Meanwhile, although the method in which the contraction of the pre-expanded particles is suppressed to minimum has been proposed as in Patent Document 3, when the contraction of the pre-expanded particles cannot be suppressed well and the pre-expanded particles contract undesirably, the bulk density thereof needs to be measured after the pre-expanded particles are made to recover from the contraction by drying them for a long period of time and so on as described above.

SUMMARY OF THE INVENTION

One or more embodiments of the invention provide a device capable of measuring bulk density of pre-expanded particles (second-stage expanded particles) with a high expansion ratio, which have the bulk density of lower than 30 g/L, in particular, for a short period of time, and a method for measuring the bulk density using the device, in the bulk density measurement for the pre-expanded particles. Further, one or more embodiments of the invention is to stably manufacture pre-expanded particles (second-stage expanded particles) having uniform bulk density without requiring selection of production conditions by visual determination or the like of shapes of the pre-expanded particles (second-stage expanded particles) by an experienced person by feeding back a measurement result of the bulk density of the obtained pre-expanded particles (second-stage expanded particles) to operating conditions of an expanding device such as a second-stage expanding machine.

It has been have found that bulk density of original pre-expanded particles (that is, before contracted) can be stably measured for a short period of time by fractionally collecting the pre-expanded particles of a constant volume, which have once contracted, in a state where they are swollen under reduced pressure, and have completed the invention.

A bulk-density measuring device for pre-expanded particles according to one or more embodiments of the invention is as follows.

[1] A bulk-density measuring device, which measures bulk density of pre-expanded particles, the device including vessel A in which contracted pre-expanded particles are capable of being swollen and recovered from contraction in a pressure-reduced state where a vessel internal pressure is lower than atmospheric pressure: vessel B which is filled with the pre-expanded particles after being swollen in vessel A in the pressure-reduced state where a vessel internal pressure is lower than the atmospheric pressure, and into which the pre-expanded particles of a constant volume are capable of being collected fractionally; a pressure-reducing unit 8 which is capable of adjusting the vessel internal pressures of vessel A and vessel B to be lower than the atmospheric pressure; and a scale 6 which is capable of measuring a weight of the pre-expanded particles filled in the vessel B.

[2] The bulk-density measuring device according to [1], further including, between vessel A and vessel B, a vessel A discharge valve 3 which is capable of discharging the pre-expanded particles accommodated in vessel A in a freely falling manner and filling vessel B with the pre-expanded panicles.

[3] The bulk-density measuring device according to [1] or [2], further including a vessel B discharge valve 4 which is capable of discharging the pre-expanded particles filled in vessel B to the scale 6.

[4] The bulk-density measuring device according to any one of [1] to [3], further including a unit which is capable of making the internal pressures of vessel A and vessel B different from each other.

[5] The bulk-density measuring device according to any one of [1] to [4], wherein vessel A has a conical portion and an angle α of the conical portion is equal to or larger than 60° and equal to or smaller than 120°.

[6] The bulk-density measuring device according to any one of [1] to [5], wherein at least one valve for controlling the vessel internal pressure is arranged on a pipe connecting vessel A and the pressure-reducing unit 8 and/or a pipe connecting vessel B and the pressure-reducing unit 8.

[7] The bulk-density measuring device according to any one of [1] to [6], wherein a forcible discharge unit 9 which is capable of forcibly discharging the pre-expanded particles filled in vessel B is provided in vessel B.

[8] The bulk-density measuring device according to any one of [1] to [7], wherein a level switch which is capable of controlling an accommodation amount of the pre-expanded particles to be accommodated is provided in vessel A.

[9] A method for measuring bulk density of pre-expanded particles, which is a method for measuring the bulk density of contracted pre-expanded particles, the method including: a) collecting a part or all of the contracted pre-expanded particles and transporting the contracted pre-expanded particles to vessel A; b) swelling the contracted pre-expanded particles so as to recover from contraction by making an internal pressure of vessel A in a pressure-reduced state lower than atmospheric pressure; c) making an internal pressure of vessel B in the pressure-reduced state lower than the atmospheric pressure; d) filling vessel B with the pre-expanded particles after being swollen in vessel A in the pressure-reduced state where the vessel internal pressure is lower than the atmospheric pressure by opening a valve 3 between vessel A and vessel B and fractionally collecting the pre-expanded particles of a constant volume; and e) measuring a weight of the pre-expanded particles by a scale 6 after the internal pressure of vessel B is returned to the atmospheric pressure and the pre-expanded particles filled in vessel B are discharged.

[10] The method for measuring the bulk density of the pre-expanded particles according to [9], wherein in the process c), the internal pressure of vessel B is set to be higher than the internal pressure of vessel A.

[11] The method for measuring the bulk density of the pre-expanded particles according to [9], wherein in the process c), the internal pressure of vessel B is set to be lower than the internal pressure of vessel A.

[12] The method for measuring the bulk density of the pre-expanded particles according to [9], wherein in the process c), the internal pressures of vessel A and vessel B are set to be equivalent.

[13] The method for measuring the bulk density of the pre-expanded particles according to any one of [9] to [12], wherein the internal pressures of vessel A and vessel B are equal to or higher than $10 \times 10^3$ Pa and equal to or lower than $90 \times 10^3$ Pa.

[14] The method for measuring the bulk density of the pre-expanded particles according to any one of [9] to [13], wherein in the process a), a bulk volume of the contracted pre-expanded particles which are transported to vessel A is equal to or higher than 20% and equal to or lower than 80% of an internal volume of vessel A.

[15] The method for measuring the bulk density of the pre-expanded particles according to any one of [9] to [14], wherein in the process d), the filling of vessel B with the pre-expanded particles is performed in a freely falling manner, and in the process e), the discharging of the pre-expanded particles from vessel B is performed at least using a forcible discharge unit 9.

[16] The method for measuring the bulk density of the pre-expanded particles according to any one of [9] to [15], wherein the pre-expanded particles are polyolefin resin pre-expanded particles.

[17] A method for manufacturing pre-expanded particles, the method including, after bulk density of the pre-expanded particles is measured by the measuring method according to any one of [9] to [16], adjusting expanding conditions of the pre-expanded particles in a pre-expanding device by comparing a measurement result and target bulk density and feeding back a result of the comparison to the pre-expanding device.

[18] The method for manufacturing the pre-expanded particles according to [17], wherein the pre-expanding device is a second-stage expanding machine.

[19] The method for manufacturing the pre-expanded particles according to [17] or [18], wherein the pre-expanded particles are polyolefin resin pre-expanded particles having bulk density of equal to or higher than 8 g/L and lower than 30 g/L.

The pre-expanded particles that are easy to contract, for example, the second-stage expanded particles with a high expansion ratio, which have a bulk density of equal to or higher than 8 g/L and lower than 30 g/L, contract immediately after manufacturing (immediately after second-stage expansion). Due to this, the original bulk density thereof cannot be measured for a short period of time after manufacturing and it takes time to perform condition setting for subsequent production. However, with the bulk-density measuring device for the pre-expanded particles and the measurement method according to the invention, the original bulk density can be stably measured for a short period of time after manufacturing.

Further, a measurement result of the bulk density is fed back to operating conditions of a pre-expanding device, for example, a second-stage expanding machine, so that the second-stage expanded particles having predetermined original bulk density can be easily manufactured.

BRIEF DESCRIPTION OF THE DRAWINGS

FIG. 2 is an entire flow diagram of the bulk-density measuring device according to one or more embodiments of the invention. In this example, automatic valves 11 and 12 are arranged, so that the internal pressures of vessel A and vessel B may be different from each other. Further, a forcible discharge unit 9 capable of blowing air into vessel B is provided. Therefore, when second-stage expanded particles accommodated in vessel B are discharged, the entire amount thereof can be discharged easily.

DESCRIPTION OF EMBODIMENTS

Hereinafter, a bulk-density measuring device according to one or more embodiments of the invention will be described with reference to FIG. 1 or FIG. 2.

It should be noted that although the following describes the case of second-stage expanded particles mainly, pre-expanded particles are not limited to the second-stage expanded particles.

Figure 1:
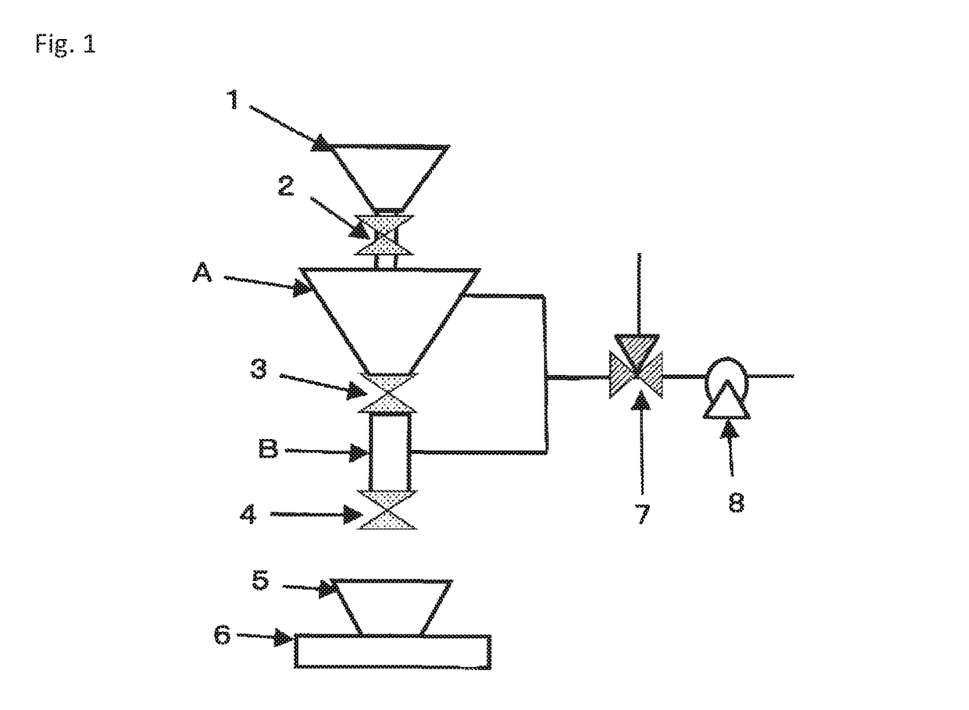
FIG. 1 is an entire flow diagram of a bulk-density measuring device according to one or more embodiments of the present invention. In this example, in-can pressures (internal pressures) of vessel A and vessel B can be made into equivalent pressure states through a three-way valve 7 by driving a pressure-reducing unit 8 (vacuum pump).
Figure 2:
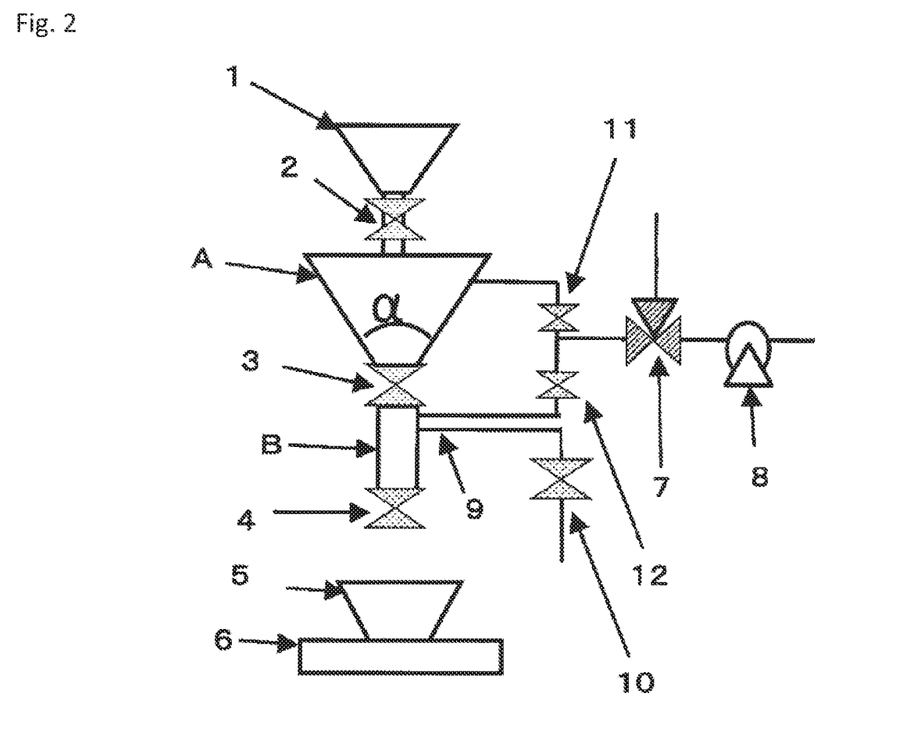

FIG. 1 and FIG. 2 schematically illustrate entire flow of the bulk-density measuring device that measures bulk density of the second-stage expanded particles immediately after being discharged from a second-stage expanding machine, as examples of embodiments of the invention.

The bulk-density measuring device according to one or more embodiments of the invention is a device including an input hopper 1 for inputting second-stage expanded particles, vessel A in which contracted second-stage expanded particles are capable of being swollen and recovered from contraction in a pressure-reduced state where a vessel internal pressure is lower than atmospheric pressure, vessel B which contains the pre-expanded particles after being swollen in vessel A in a pressure-reduced state where a vessel internal pressure is lower than atmospheric pressure, and into which the pre-expanded particles of a constant volume are capable of being fractionally collected, a pressure-reducing unit 8 which is capable of adjusting the vessel internal pressures of vessel A and vessel B to be lower than the atmospheric pressure, and a scale 6 which is capable of measuring a weight of the pre-expanded particles contained in vessel B. Vessel A and vessel B are examples of "the first vessel" and "second vessel," respectively.

The input hopper 1 is a hopper for inputting the second-stage expanded particles discharged from the second-stage expanding machine into vessel A.

A shape of the input hopper 1 is not particularly limited as long as the input hopper 1 is configured so as not to cause the second-stage expanded particles to remain in the hopper. In particular, a conical shape may be used because it does not cause the second-stage expanded particles to remain.

Although a volume of the input hopper 1 is not particularly limited, it may be at least a half of the volume of vessel B and equal to or smaller than 5 times the volume of vessel B, which will be described later, and may be equal to or larger than 1.5 times and equal to or smaller than 4 times the volume of vessel B. If the volume of the input hopper is smaller than half the volume of vessel B, an amount of the second-stage expanded particles is small and measurement accuracy of the bulk density tends to be lower. On the other hand, if the volume of the input hopper is larger than 5 times the volume of vessel B, the device itself is increased in size and the cost thereof tends to be increased.

Vessel A is a vessel in which contracted second-stage expanded particles are capable of being swollen and recovered from the contraction in the pressure-reduced state where the vessel's internal pressure is lower than the atmospheric pressure.

There arises no problem when vessel A has a shape that does not cause the swollen second-stage expanded particles as a measurement sample to remain in vessel A at the time of discharge. Vessel A has a conical shape and may have no cylindrical body portion.

An angle α (see FIG. 2) of a conical portion of vessel A may be equal to or larger than 60° and equal to or smaller than 120°, such as equal to or larger than 80° and equal to or smaller than 100°.

If the angle α of the conical portion of vessel A is smaller than 60°, when the second-stage expanded particles are swollen at a pressure lower than the atmospheric pressure, the second-stage expanded particles push with one another and are also pushed by the inner walls of vessel A. Due to this, the second-stage expanded particles are excessively clogged tightly in vessel A and obstruction may more easily occur. Therefore, the second-stage expanded particles may not be easily discharged into vessel B. On the other hand, if the angle α is larger than 120°, the second-stage expanded particles are difficult to slide or roll in vessel A and may more easily remain. Also in this case, the second-stage expanded particles tend to be difficult to be discharged into vessel B from vessel A.

Although the volume of vessel A is not particularly limited, it may be equal to or larger than one time and equal to or smaller than 5 times the volume of vessel B, which will be described later, and may be equal to or larger than 2 times and equal to or smaller than 4 times the volume of vessel B. If the volume of vessel A is smaller than one time the volume of vessel B, the amount of the second-stage expanded particles is small and the measurement accuracy of the bulk density tends to lower. On the other hand, if the volume of vessel A is larger than five times the volume of vessel B, the device itself is increased in size and cost thereof tends to be increased.

A vessel A input valve 2 and a vessel A discharge valve 3 can be provided on an upper end portion and a lower end portion of vessel A, respectively.

An aperture of vessel A input valve 2 is not particularly limited as long as it has a size preventing the second-stage expanded particles from causing an obstruction. For example, when a diameter of the second-stage expanded particles is approximately 5 mm, the second-stage expanded particles can be collected without causing an obstruction by setting the aperture of vessel A input valve 2 equal to or larger than 20A (inner diameter of approximately 20 mm). When the diameter of the second-stage expanded particles is approximately 10 mm, the second-stage expanded particles can be collected without causing an obstruction by setting the aperture of vessel A input valve 2 equal to or larger than 50A (inner diameter of approximately 50 mm).

The vessel A discharge valve 3 can be provided between vessel A and vessel B.

It is sufficient that the aperture of vessel A discharge valve 3 has a size preventing the swollen second-stage expanded particles from causing an obstruction. For example, when a diameter of the swollen second-stage expanded particles is approximately 8 mm, it is sufficient that the aperture of the vessel A discharge valve 3 is set equal to or larger than 20A (inner diameter of approximately 20 mm). For example, when the diameter of the swollen second-stage expanded particles is approximately 13 mm, the second-stage expanded particles can be transported without causing an obstruction by setting the aperture of the vessel A discharge valve 3 equal to or larger than 50A (inner diameter of approximately 50 mm).

Although the input hopper 1 for inputting the second-stage expanded particles discharged from the second-stage expanding machine into vessel A is provided in the above description as an example, the input hopper 1 is not necessarily required to be provided. For example, the second-stage expanded particles can be also input into vessel A without passing through the input hopper 1 by connecting a transportation hose to vessel A input valve 2, pneumatically transporting the second-stage expanded particles through the transportation hose, and so on.

A level switch capable of controlling an accommodation amount of the second-stage expanded particles to be accommodated may be provided in vessel A. The accommodation amount that is controlled by the level switch also depends on a contraction rate of the second-stage expanded particles to be input, the shape of vessel A, and the like. Although it is sufficient that the accommodation amount is adjusted appropriately, the second-stage expanded particles of equal to or higher than 20% and equal to or lower than 80% of the volume of vessel A are set to be accommodated. If the accommodation amount is lower than 20% of the volume of vessel A, the amount of the second-stage expanded particles does not reach an amount enough to fill vessel B in some cases. If the accommodation amount is higher than 80%, when the pressure is reduced and the second-stage expanded particles swell, an obstruction tends to occur in vessel A.

Vessel B is a vessel which is filled with the second-stage expanded particles after being swollen in vessel A in the pressure-reduced state where a vessel's internal pressure is lower than the atmospheric pressure and in which the second-stage expanded particles of a constant volume are fractionally collected. Vessel B can be connected to vessel A through the vessel A discharge valve 3, for example.

Although a shape of vessel B is not particularly limited as long as vessel B is configured so as to fill vessel B with the swollen second-stage expanded particles as tight as possible, it may be a cylindrical shape.

Although the volume of vessel B is not particularly limited, it may be equal to or larger than 0.1 L and equal to or smaller than 30 L, such as equal to or larger than 0.5 L and equal to or smaller than 20 L.

If the volume of vessel B is smaller than 0.1 L, accuracy of the bulk density to be measured tends to be lower.

If the volume of vessel B is larger than 30 L, the device itself is increased in size and the cost thereof tends to be increased. In addition, a large installation space is required, and the device tends to be installed in a large site only.

It is sufficient that the volume of vessel B is obtained by filling vessel B with water in a sealed manner and measuring a volume of the water in this case, and the volume of vessel B is set to V(L).

An upper end portion of vessel B is connected to vessel A through vessel A discharge valve 3 and a vessel B discharge valve 4 can be provided on a lower end portion thereof. It is sufficient that an aperture of vessel B discharge valve 4 has a size preventing the second-stage expanded particles from causing an obstruction. For example, when a diameter of the second-stage expanded particles is approximately 8 mm, it is sufficient that the aperture of vessel B discharge valve 4 is set equal to or larger than 20A (inner diameter of approximately 20 mm). For example, when the diameter of the second-stage expanded particles is approximately 13 mm, the second-stage expanded particles can be transported without causing an obstruction by setting the aperture of vessel B discharge valve 4 equal to or larger than 50A (inner diameter of approximately 50 mm).

It should be noted that observation windows may be provided on the side surfaces of vessel A and vessel B because swelling and contraction states and a discharge state of the second-stage expanded particles can be checked therethrough.

The pressure-reducing unit 8 is not particularly limited as long as it can adjust the internal pressures of vessel A and vessel B to be lower than the atmospheric pressure ($\approx 10^5$ Pa).

Ultimate pressure of the pressure-reducing unit 8 may be equal to or higher than 1 Pa and equal to or lower than $20 \times 10^3$ Pa. If the ultimate pressure of the pressure-reducing unit 8 is lower than 1 Pa, the degrees of vacuum in vessel A and vessel B are increased but the device itself tends to be increased in cost. If the ultimate pressure of the pressure-reducing unit 8 is higher than $20 \times 10^3$ Pa, the contracted second-stage expanded particles as the measurement sample cannot be sufficiently swollen when airtightness of the vessel is lowered. This results in tendency that the measurement accuracy of the bulk density lowers.

Vessel A, vessel B, and the pressure-reducing unit 8 (for example, vacuum pump) are coupled with pipes and a valve 7 (for example, three-way valve) can be installed between a merging portion of the pipes connected to vessel A and vessel B and the pressure-reducing unit 8. Meshes are provided on connection holes of the pipes to vessel A side and vessel B side. A wire diameter and a sieve size of the meshes are not particularly limited as long as the second-stage expanded particles cannot pass through the meshes and only the air sucked by a vacuum pump can pass through the meshes.

In the above-mentioned example, pressures in vessel A and vessel B are reduced by one pressure-reducing unit 8. Alternatively, independent pressure-reducing units 8 can be also provided on vessel A and vessel B.

In the method for measuring the bulk density of the contracted pre-expanded particles according to one or more embodiments of the invention, vessel A and vessel B are made into the pressure-reduced states where the internal pressures thereof are lower than the atmospheric pressure.

Although the internal pressures of vessel A and vessel B are not particularly limited as long as they are lower than the atmospheric pressure, the internal pressures as absolute pressures may be equal to or higher than $10 \times 10^3$ Pa and equal to or lower than $90 \times 10^3$ Pa, such as equal to or higher than $10 \times 10^3$ Pa and equal to or lower than $60 \times 10^3$ Pa. or equal to or higher than $10 \times 10^3$ Pa and equal to or lower than $30 \times 10^3$ Pa.

If the internal pressures of vessel A and vessel B are lower than $10 \times 10^3$ Pa, the internal pressures of vessel A and vessel B are decreased but the pressure reducing device tends to be increased in cost. If the internal pressures of vessel A and vessel B are higher than $90 \times 10^3$ Pa, the internal pressures are increased and the contracted second-stage expanded particles as the measurement sample cannot be sufficiently swollen. Due to this, accuracy of the bulk density tends to be lower.

The internal pressures of vessel A and vessel B may be set to be different or the same. When the internal pressures of vessel A and vessel B are set to be different, the internal pressure of vessel B may be set to be higher than or lower than the internal pressure of vessel A.

In the case where the internal pressure of vessel B is set to be higher than the internal pressure of vessel A, when vessel A discharge valve 3 is opened in order to transport the second-stage expanded particles that have been swollen and recovered from contraction in vessel A to vessel B, the air is once ejected to vessel A side from vessel B side. In this case, even when the second-stage expanded particles cause an obstruction in the vicinity of the bottom of vessel A, the obstruction is dissolved by pressure difference (ejection of the air). Thereafter, vessel B may be more easily filled with the second-stage expanded particles by free fall and a filling state in vessel B becomes stable, so that measurement error is reduced. Accordingly, the case where the internal pressure of vessel B is set to be higher than the internal pressure of vessel A is disclosed according to one or more embodiments.

As the pressure difference when the internal pressure of vessel B is set to be higher in the case where the internal pressures of vessel A and vessel B are made different from each other, a range equal to or higher than $5 \times 10^3$ Pa and equal to or lower than $30 \times 10^3$ Pa is disclosed, such as a range equal to or higher than $7 \times 10^3$ Pa and equal to or lower than $15 \times 10^3$ Pa. When the pressure difference is within the range above, the obstruction with the second-stage expanded particles is easily dissolved in the vicinity of the bottom of vessel A and re-contraction of the pre-expanded particles after vessel A discharge valve 3 is opened may not readily occur. Therefore, the bulk density can be measured accurately.

By contrast, it may be that the internal pressure of vessel B be set to be lower than the internal pressure of vessel A because the obstruction is dissolved by pressure difference (ejection of the air) even when the second-stage expanded particles cause the obstruction in the vicinity of the bottom of vessel A. Note that the obtained bulk density tends to be higher than the original bulk density in this case. Accordingly, the case where the internal pressure of vessel B is higher than the internal pressure of vessel A is disclosed.

As the pressure difference when the internal pressure of vessel A is set to be higher in the case where the internal pressures of vessel A and vessel B are made different from each other, a range equal to or higher than $5 \times 10^3$ Pa and equal to or lower than $30 \times 10^3$ Pa may be used, such as a range equal to or higher than $5 \times 10^3$ Pa and equal to or lower than $10 \times 10^3$ Pa. When the pressure difference is within the range above, the obstruction with the second-stage expanded particles may easily be dissolved in the vicinity of the bottom of vessel A and re-contraction of the pre-expanded particles after vessel A discharge valve 3 is opened may be not easily occur. Therefore, the bulk density can be measured accurately.

A mode in which the internal pressures of vessel A and vessel B are made the same (equivalent) is disclosed according to one or more embodiments for the following reason.

That is, the internal pressures of vessel A and vessel B can be made the same (equivalent) through the three-way valve 7 by driving the pressure-reducing unit 8 in a state where the valves 2, 3, and 4 are closed as illustrated in FIG. 1. Because a unit for making the internal pressures of vessel A and vessel B different is not required to be provided and facility design is easy.

It should be noted that when the internal pressures of vessel A and vessel B are made the same (equivalent), the shape of vessel A, the aperture of vessel A discharge valve 3, and the like are required to be examined sufficiently and adjustment needs to be performed in order to sufficiently suppress the obstruction with the second-stage expanded particles in the vicinity of the bottom of vessel A.

In the bulk-density measuring device according to one or more embodiments of the invention, a unit that adjusts the internal pressures of vessel A and vessel B is not particularly limited. Examples thereof include:

(A) as illustrated in FIG. 2, a method in which pressure gauges and/or pressure sensors (not illustrated) are previously attached to vessel A and vessel B, and a valve 11 provided on the pipe between the three-way valve 7 and vessel A and a valve 12 provided on the pipe between the three-way valve 7 and vessel B are closed at a time point at which desired pressures have been obtained;

(B) as illustrated in FIG. 2, a method in which the internal pressure of vessel B is adjusted by connecting a forcible discharge unit 9 (pipe), which will be described later, and a valve 10 to vessel B, reducing the pressure in vessel B to certain pressure, and then, opening the valve 10 appropriately;

(C) as illustrated in FIG. 2, a method in which the internal pressure of vessel A is adjusted by reducing the pressure in vessel A to certain pressure, and then, opening the valve 2 appropriately; and (D) as illustrated in FIG. 2, a method in which the internal pressure of vessel A is adjusted by reducing the pressure in vessel A to certain pressure, and then, opening the valve 11 and the valve 7 appropriately.

In method (A), a method using automatic valves that are automatically closed at a time point where desired pressures in vessels A and B have been obtained.

The scale 6 is a device that measures a weight of the second-stage expanded particles discharged from vessel B through vessel B discharge valve 4. The scale 6 captures the discharged second-stage expanded particles without exception by installing a discharge receiving tray 5 and so on and measures the weight thereof.

In the measurement of the weight of the second-stage expanded particles, the forcible discharge unit 9 may be provided such that the second-stage expanded particles can be completely discharged from vessel B.

The forcible discharge unit 9 can employ a method in which a pipe is connected to vessel B and the air is ejected from the pipe so as to forcibly discharge the second-stage expanded particles from vessel B using the air when the second-stage expanded particles are discharged through vessel B discharge valve 4. With the method, even in a state where the second-stage expanded particles are charged and are difficult to be discharged from vessel B, the second-stage expanded particles can be discharged efficiently.

The bulk density measurement for the pre-expanded particles, in particular, the second-stage expanded particles using the bulk-density measuring device can be performed with the following processes.

That is to say, the method for measuring the bulk density of the pre-expanded particles using the bulk-density measuring device includes:

(a) collecting a part or all of the contracted pre-expanded particles and transporting the contracted pre-expanded particles to vessel A;

(b) swelling the contracted pre-expanded particles so as to recover from contraction by making the internal pressure of vessel A in the pressure-reduced state lower than the atmospheric pressure;

(c) making the internal pressure of vessel B in the pressure-reduced state lower than the atmospheric pressure;

(d) filling vessel B with the pre-expanded particles after being swollen in vessel A in the pressure-reduced state where the vessel internal pressure is lower than the atmospheric pressure by opening the valve 3 between vessel A and vessel B, and fractionally collecting the pre-expanded particles of a constant volume; and (e) measuring the weight of the pre-expanded particles by the scale 6 after the internal pressure of vessel B is returned to the atmospheric pressure and the pre-expanded particles filled in vessel B are discharged.

In a bulk-density measuring operation for the pre-expanded particles (second-stage expanded particles) using the bulk-density measuring device, the second-stage expanded particles attach to inner wall portions of the input hopper, vessel A, and vessel B and the particles repel one another with static electricity or the like, and the accurate bulk density cannot be measured in some cases.

In this case, the following processing of removing static electricity is performed before the measurement operation, thereby measuring the bulk density normally. Specific measures of the static electricity removal method include, for example, a method in which an antistatic agent is added (sprayed) to the second-stage expanded particles, a method in which the bulk-density measuring device is grounded (connected to the ground), or a method in which the static electricity is forcibly removed with ejection of compressed air or the like (for example, the above-described forcible discharge unit 9).

A commercially available antistatic agent, surfactant, or the like can be used as the antistatic agent.

As described above, usage of the bulk-density measuring device enables the original bulk density to be calculated by swelling the second-stage expanded particles immediately after being discharged from the second-stage expanding machine at a pressure lower than the atmospheric pressure, collecting them as samples into the vessel having a constant volume, and measuring the weight of the second-stage expanded particles having the constant volume.

A bulk density measurement result by the bulk-density measuring device is input to a personal computer, a sequencer, or the like as an electric signal and is subjected to a comparison operation with a target bulk density value using bulk density comparison operation software. With this, the bulk density measurement result can be utilized for controlling manufacturing conditions of the pre-expanded particles or the second-stage expanded particles.

For example, with a method for manufacturing pre-expanded particles as disclosed in JP-A No. 2009-161738, time (expansion time) taken to discharge the expanded particles to a pressure area lower than the internal pressure of a sealed vessel reaches equal to or longer than several minutes in some cases. When the bulk density measurement result at a certain time point is different from target bulk density, a signal of new pressure or temperature set value is transmitted to a pressure setting device, a temperature setting device, or the like controlling pressure, a temperature, or the like in the sealed vessel so as to obtain the target bulk density. Thus, the bulk density can be controlled continuously while the expanded particles are discharged into the low pressure area.

On the other hand, with a method for manufacturing pre-expanded particles or a method for manufacturing second-stage expanded particles as disclosed in JP-A No. 2009-263639, when a bulk density measurement result of a certain batch (shot) is different from target bulk density, a signal of a new pressure set value is transmitted to a pressure setting device controlling an in-can heating steam pressure in a pre-expanding machine or a second-stage expanding machine so as to obtain the target bulk density, and is fed back to subsequent batch manufacturing conditions. With this, the bulk density can be controlled continuously.

To be specific, when the bulk density of the pre-expanded particles or the second-stage expanded particles obtained at a certain time point is higher than the target bulk density, a set value signal higher than heating steam pressure in a previous batch is transmitted in a subsequent batch in order to make the bulk density lower. On the other hand, when the bulk density thereof is lower than the target bulk density, a set value signal lower than the heating steam pressure in the previous batch is transmitted so as to obtain pre-expanded particles or second-stage expanded particles having bulk density of a certain range, which is approximate to the target bulk density.

It should be noted that well-known software can be used as bulk density comparison operation software.

As a method for manufacturing the pre-expanded particles that are subjected to the bulk-density measuring device, a conventionally well-known manufacturing method can be employed.

For example, as disclosed in the above-mentioned JP-A No. 2009-161738, exemplified is a method for manufacturing thermoplastic resin expanded particles (pre-expanded particles) using water and/or carbon dioxide or the like contained in an aqueous dispersion medium as an expanding agent. The method includes dispersing thermoplastic resin particles in the aqueous dispersion medium in the sealed vessel, heating and pressurizing them to a temperature of equal to or higher than a softening temperature of the thermoplastic resin particles, and then, releasing them to a pressure range lower than the internal pressure of the sealed vessel. The method is particularly preferable when polyolefin resin pre-expanded particles are manufactured.

Further, as disclosed in the above-mentioned JP-A No. 2009-263639, exemplified is a method for manufacturing pre-expanded particles having predetermined bulk density. The method includes impregnating thermoplastic resin particles polymerized in a polymerization vessel with an expanding agent to obtain expandable thermoplastic resin particles, and then, heating them with a heating medium such as steam using a pre-expanding machine or the like. The method is particularly preferable when polystyrene resin pre-expanded particles and styrene modified polyolefin resin pre-expanded particles are manufactured.

The pre-expanded particles obtained in this manner can also be used to form pre-expanded particles (second-stage expanded particles) having a higher expansion ratio using a second-stage expanding machine.

Examples of the method for manufacturing the second-stage expanded particles that are used in the bulk-density measuring device include a method in which internal pressure is previously applied to pre-expanded particles obtained separately and the provided pre-expanded particles are input to a can of a second-stage expanding machine so as to be made contact with heated steam. These methods can provide the second-stage expanded particles having an expansion ratio higher than that of the pre-expanded particles.

It should be noted that the application of the internal pressure to the pre-expanded particles can be performed easily by a conventionally well-known method such as a method including filling a pressure-resistant sealed vessel with the pre-expanded particles and performing pressurizing processing with the air or the like. Further, multiple-stage expanded particles, such as third-stage expanded particles, can also be provided by repeating the method for manufacturing the second-stage expanded particles.

Examples of resin as a base material of the pre-expanded particles that are used include polypropylene resin, polyethylene resin, ethylene-vinyl acetate copolymer resin, polystyrene resin, impact-resistant polystyrene resin, styrene-(meth)acrylic acid copolymer resin, acrylonitrile-styrene copolymer resin, methacrylic acid ester resin, vinylidene chloride resin, polyphenylene ether resin, and a mixture thereof. Examples of the mixture include mixed resin of polyphenylene ether and polystyrene, composite resin in which vinylic monomer is graft copolymerized with a part of polyolefin (styrene modified polyolefin resin), and the like.

In a point of further exertion of an effect that the pre-expanded particles with uniform bulk density are obtained in the invention, the polyolefin resin such as the polypropylene resin and the polyethylene resin may be used as the base resin of the pre-expanded particles, and the bulk-density measuring device may be used for manufacturing the second-stage expanded particles thereof. In the second-stage expansion of polyolefin resin pre-expanded particles such as polypropylene resin pre-expanded particles and polyethylene resin pre-expanded particles, bulk density changes sensitively relatively with second-stage expansion set pressure and the second-stage expansion set pressure for each batch is therefore required to be adjusted frequently and accurately. The bulk-density measuring device enables them to be controlled easily, thereby obtaining the second-stage expanded particles having uniform bulk density.

The bulk density of the polyolefin resin pre-expanded particles is not particularly limited. However, the polyolefin resin pre-expanded particles having bulk density of equal to or higher than 8 g/L and lower than 30 g/L with multiple-stage expansion such as the second-stage expansion are easy to contract with the multiple-stage expansion and variation in the bulk density thereof is easy to be increased. As for this point, the system described herein can control the bulk density continuously by measuring the bulk density of the pre-expanded particles after being swollen and recovered from the contraction and feeding back the result thereof to the subsequent batch manufacturing conditions, thereby performing stable multiple-stage expansion with uniform bulk density. Therefore, the above-mentioned polyolefin resin pre-expanded particles may be used.

As a method for obtaining the polypropylene resin pre-expanded particles or the polyethylene resin pre-expanded particles, specifically, the existing method as disclosed in JP-A No. 2009-161738 can be employed.

For example, a polyolefin resin composition formed with polypropylene resin or polyethylene resin is used for polyolefin resin particles and the polyolefin resin particles are expanded, thereby obtaining the polyolefin resin pre-expanded particles.

The polyolefin resin composition is a resin composition by using polyolefin resin as a main material and blending a hydrophilic substance such as polyethylene glycol, glycerin, and melamine if necessary. The polyolefin resin composition is molten using an extruder or the like so as to obtain polyolefin resin particles having a desired particle shape such as a cylindrical shape.

A dispersion obtained by dispersing the polyolefin resin particles together with an expanding agent such as carbon dioxide in water in a sealed vessel is heated to a temperature in a range of a melting point −20° to a melting point +20° of the polyolefin resin particles so as to impregnate the polyolefin resin particles with the expanding agent. Then, the polyolefin resin particles are released to an atmosphere of a pressure lower than that in the vessel while the temperature and the pressure in the vessel are kept to be constant under the pressure of equal to or higher than steam pressure by the expanding agent. With this, the original polyolefin resin pre-expanded particles are obtained.

Examples of the polyolefin resin include polypropylene resin such as homopropylene resin, propylene-ethylene random copolymer, propylene-butene random copolymer, and propylene-ethylene-butene terpolymer, and polyethylene resin such as high-density polyethylene resin, medium-density polyethylene resin, low-density polyethylene resin, and straight chain low-density polyethylene resin.

EXAMPLES

Hereinafter, although the invention will be further described with examples, the invention is not limited to the examples.

Example 1

<Production of Resin Particles>

With 100 parts by weight of straight chain low-density polyethylene resin [MI=2.0 g/10 min, melting point 122° C.], 0.2 parts by weight of glycerin [purified glycerin D manufactured by Lion Corporation] and 0.03 parts by weight of talc were dry-blended. The blend was supplied to a 50 φ single screw extruder at a discharge rate of 40 kg/hr, molten and kneaded at a resin temperature of 220° C., cooled with water, and then, cut with a pelletizer so as to obtain straight chain low-density polyethylene resin particles (4.5 mg/particle) having cylindrical shapes.

<Production of First-Stage Expanded Particles>

100 parts by weight of the obtained straight chain low-density polyethylene resin particles, 200 parts by weight of pure water, 0.5 parts by weight of tertiary calcium phosphate, and 0.05 parts by weight of sodium n-paraffin sulfonate were put in the pressure-resistant sealed vessel, and 7.5 parts by weight of carbon dioxide was introduced into the pressure-resistant sealed vessel while stirring the mixture. The obtained mixture was heated to 122° C. and held for 30 minutes. Pressure in the pressure-resistant sealed vessel at this time was 3.5 MPa (gauge pressure).

Thereafter, a valve on a lower portion of the sealed vessel was opened and the mixture was released to the atmospheric pressure through an orifice plate so as to obtain polyethylene resin pre-expanded particles having bulk density of 60 g/L.

<Production of Second-Stage Expanded Particles>

After the obtained polyethylene resin pre-expanded particles were dried, they were put into the pressure-resistant vessel, and the internal pressure thereof was set to 0.39 MPa (absolute pressure) using the pressurized air. Then, the obtained polyethylene resin pre-expanded particles were put into the can of the second-stage expanding machine and were heated in a contact manner with heating steam of 0.07 MPa (gauge pressure) for 30 seconds, thereby manufacturing the second-stage expanded particles. The obtained second-stage expanded particles had contracted.

<Bulk Density Measurement for Second-Stage Expanded Particles>

The bulk density of the second-stage expanded particles discharged from the second-stage expanding machine was measured using the bulk-density measuring device as illustrated in FIG. 1.

(a) The contracted second-stage expanded particles were put into the input hopper 1 (volume 3 L) until it was substantially filled with them in a state where the vessel A input valve 2 was closed.

Subsequently, in a state where the vessel A input valve 2 (inner diameter 50 mm) was opened and the vessel A discharge valve 3 was closed, the second-stage expanded particles were put in vessel A (volume 4 L, angle of the conical portion α=90°) and the vessel A input valve 2 was closed.

(b) Thereafter, the closed state of the vessel B discharge valve 4 was checked, and then, the pressure-reducing unit 8 (vacuum pump) was driven so as to reduce the internal pressures of vessel A and vessel B to $30 \times 10^3$ Pa in a pressure-equalized state through the three-way valve 7. Thus, the second-stage expanded particles in vessel A were swollen.

(c) The three-way valve 7 was operated to block connection to the pressure-reducing unit 8 while the internal pressures of vessel A and vessel B were kept to $30 \times 10^3$ Pa. Thereafter, the vessel A discharge valve 3 was opened and the second-stage expanded particles that had been swollen in vessel A were transported and filled into vessel B having the volume V=1 L in a freely falling manner. Then, the vessel A discharge valve 3 was closed.

(d) After that, the three-way valve 7 was operated to return the internal pressures of vessel A and vessel B to the atmospheric pressure. Then, the second-stage expanded particles that had been swollen in vessel B were contracted to the original second-stage expanded particles.

Subsequently, the vessel B discharge valve 4 was opened and total amount of the second-stage expanded particles was discharged to the discharge receiving tray 5. Then, the weight [W(g)] of the discharged particles was measured using the scale 6 so as to calculate the bulk density [W/V (g/L)].

<Feedback to Second-Stage Expanding Machine>

Then, the measurement result as the above-mentioned calculated result and a target value were compared using the bulk density comparison operation device composed of a personal computer incorporating an analog signal input and output terminal.

A measured value of the bulk density of a first batch (shot) of the second-stage expansion was 14 g/L which is higher than 12 g/L as a median value of the target value of 10 to 14 g/L. Then, a signal increasing the set pressure of the heating steam pressure of the second-stage expanding machine was transmitted to the pressure setting device. After that, the bulk density of the second-stage expanded particles was measured for every even-numbered shot and modified signals were transmitted until an eightieth shot so as to make the bulk density close to the target median value. In this manner, adjustment was continued.

When the second-stage expansion for 80 shots was executed, the bulk densities from the first shot to the eightieth shot were within the target value of 10 to 14 g/L and stable. However, obstruction with the second-stage expanded particles occurred once in vessel A. In this case, the bulk density measurement was interrupted to dissolve the obstruction with the second-stage expanded particles in vessel A. Then, the measurement was restarted.

Figure 4:
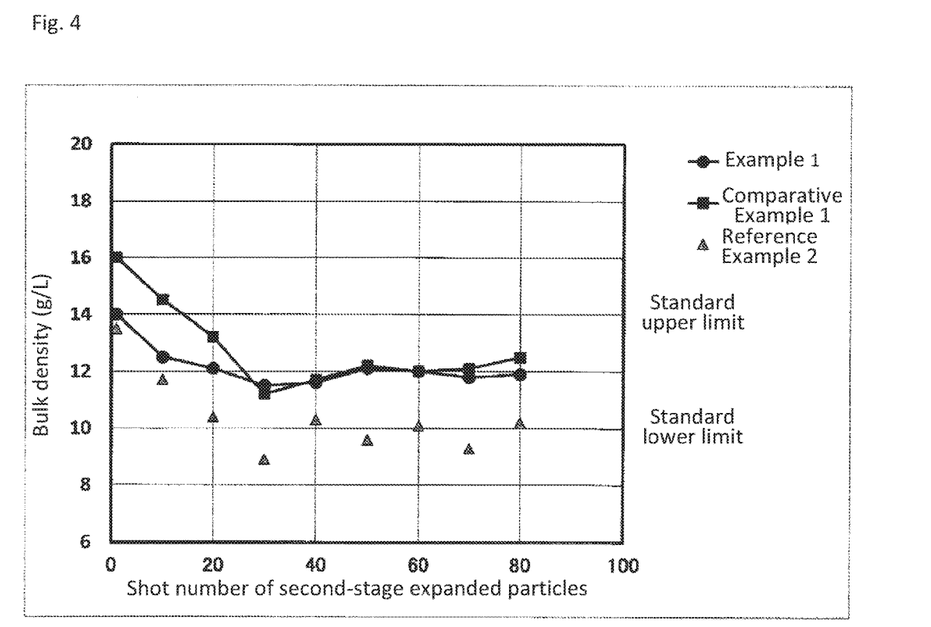
FIG. 4 is a graph illustrating (i) change of bulk density of second-stage expanded particles for each shot based on results of a bulk density measurement measured for the second-stage expanded particles by the bulk-density measuring device according to one or more embodiments of the present invention, and (ii) change in bulk density of second-stage expanded particles for each shot based on results of a bulk-density measurement measured for the second-stage expanded particles by a bulk-density measuring device according to a conventionally known bulk-density measuring device. The aforementioned (i) and (ii) respectively correspond to Example 1 and Comparative Example 1. In Example 1, the second-stage expanded particles were manufactured in such a manner that the bulk density of the second-stage expanded particles for each batch (each shot) is adjusted by feeding back, to second-stage expansion manufacturing conditions, results of a bulk-density measurement of the second-stage expanded particles using the bulk-density measure device according to one or more embodiments of the present invention. In Comparative Example 1, the second-stage expanded particles were manufactured in such a manner that the bulk density of the second-stage expanded particles is adjusted by feeding back, to second-stage expansion manufacturing conditions, results of a bulk density measurement of the second-stage expanded particles using a conventionally known bulk-density measuring device. Further, the bulk density of the second-stage expanded particles after the heating process, which were obtained in the comparative example, is also illustrated.

The bulk density measurement results and conditions of the two-stage expansion for every ten shots are indicated in Table 1, Table 2, and FIG. 4.

Reference Example 2

The second-stage expanded particles collected in Comparative Example 1 were left to stand for four hours in a dryer adjusted at 80° C. in order to recover them from

TABLE 1

Bulk density measurement result

| | | | Shot number | | | | | | | | |
|---|---|---|---|---|---|---|---|---|---|---|---|
| | | | 1 | 10 | 20 | 30 | 40 | 50 | 60 | 70 | 80 |
| Example 1 | | Bulk density (g/L) | 14 | 12.5 | 12.1 | 11.5 | 11.6 | 12.1 | 12 | 11.8 | 11.9 |
| Comparative Example 1 | | Bulk density (g/L) | 16 | 14.5 | 13.2 | 11.2 | 11.7 | 12.2 | 12 | 12.1 | 12.5 |
| Reference Example 1 | Heat processing on Example 1 | Bulk density (g/L) | 14 | 12.4 | 12.2 | 11.6 | 11.6 | 12 | 12.1 | 12 | 12 |
| Reference Example 2 | Heat processing on Comparative Example 1 | Bulk density (g/L) | 13.5 | 11.7 | 10.4 | 8.9 | 10.3 | 9.6 | 10.1 | 9.3 | 10.2 |

Production standard 10 to 14 g/L

Comparative Example 1

Figure 3:
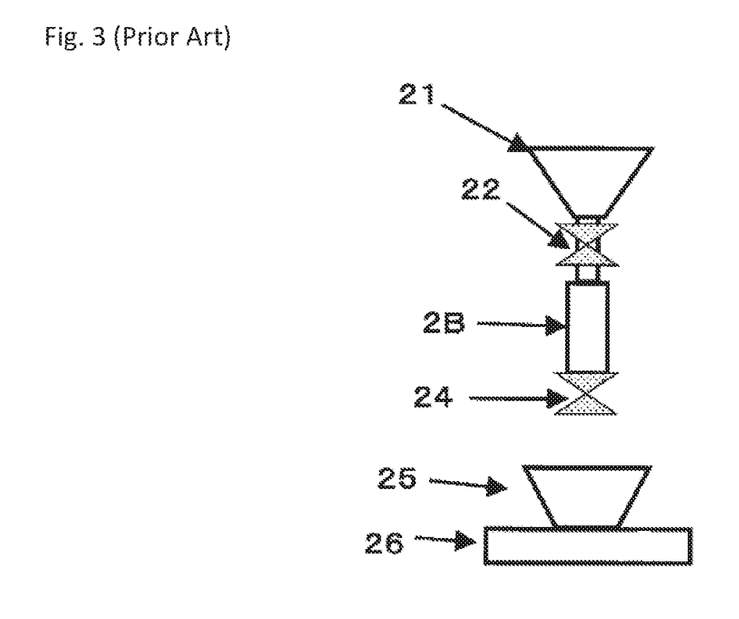
FIG. 3 is an entire flow diagram in a conventional bulk-density measuring device.

The bulk density of the second-stage expanded particles produced in Example 1 was measured using a well-known bulk-density measuring device as illustrated in FIG. 3, which has been conventionally known. The well-known bulk-density measuring device is a device that has a configuration in which vessel B is connected to an input hopper 21 through an input valve 22 and that fractionally collects the second-stage expanded particles under the atmospheric pressure.

When the conventional bulk density device was used, the bulk density of a first shot of the second-stage expansion was 16 g/L which is higher than the target value of 10 to 14 g/L. Then, the signal to increase heating steam pressure of the second-stage expanding machine was transmitted to the pressure setting device. The bulk density of the second-stage expanded particles was measured for every ten shots and modified signals were transmitted until the eightieth shot so as to make the bulk density close to the target median value. In this manner, adjustment was continued.

The bulk density measurement results thereof are illustrated in Table 1, Table 2, and FIG. 4.

Reference Example 1

The second-stage expanded particles collected in Example 1 were left to stand for four hours in a dryer adjusted at 80° C. in order to recover them from contraction. After that, the bulk density of the second-stage expanded particles was measured using the well-known bulk-density measuring device as illustrated in FIG. 3.

The bulk density measurement results thereof are illustrated in Table 1.

The bulk densities of the second-stage expanded particles that were left to stand for four hours in the dryer adjusted at 80° C. and had been recovered from the contraction indicate similar values as the bulk densities (Example 1) measured by the bulk-density measuring device. In other words, the bulk densities within the target value were obtained. That is to say, it is found that the bulk density measured by the bulk-density measuring device could be measured as the bulk density of the original second-stage expanded particles.

contraction. After that, the bulk density of the second-stage expanded particles was measured using the well-known bulk-density measuring device as illustrated in FIG. 3.

The bulk density measurement results thereof are illustrated in Table 1 and FIG. 4.

The bulk densities of the second-stage expanded particles that were left to stand for four hours in the dryer adjusted at 80° C. and had been recovered from the contraction were lower than the bulk densities (Comparative Example 1) of the second-stage expanded particles in the contracted state, which were measured by the conventional bulk-density measuring device. That is to say, it is found that the bulk densities (Comparative Example 1) of the second-stage expanded particles, which were measured by the conventional method, are different from the bulk densities (Reference Example 2) of the original second-stage expanded particles. Further, the bulk densities were deviated from the target bulk density and variation thereof was large.

As is clearly seen from the measurement result of a first shot in Table 1, the measurement value by the conventionally well-known bulk-density measuring device was high because of the contraction whereas the original bulk density could be measured by the bulk-density measuring device with excellent reproducibility because the second-stage expanded particles were swollen under the reduced pressure and recovered into the original states of the expanded particles.

As for feedback results based on the measurement results of the bulk densities, as indicated in Table 1 and FIG. 4, the bulk densities of the second-stage expanded particles from the first shot to the eightieth shot when the bulk-density measuring device was used were within the target value of 10 to 14 g/L and stable.

On the other hand, when the conventionally well-known bulk-density measuring device was used, the second-stage expanded particles discharged from the second-stage expanding machine contracted and the original bulk densities could not be measured. As a result, the bulk densities were largely varied among the shots. Further, the bulk densities of the second-stage expanded particles that had been recovered from the contraction by the heating process were also varied largely.

TABLE 2

|  |  | Example | | | | |
|---|---|---|---|---|---|---|
|  |  | 1 | 2 | 3 | 4 | 5 |
| Angle α of conical portion | ° | 90 | 90 | 60 | 50 | 130 |
| Internal pressure of vessel A immediately before filling into vessel B | Pa | $30 \times 10^3$ | $20 \times 10^3$ | $20 \times 10^3$ | $20 \times 10^3$ | $20 \times 10^3$ |
| Internal pressure of vessel B immediately before filling into vessel B | Pa | $30 \times 10^3$ | $30 \times 10^3$ | $30 \times 10^3$ | $30 \times 10^3$ | $30 \times 10^3$ |
| Conditions of second-stage expanded particles |  | Obstruction occurred once in vessel A in 80 shots. | No problem. | No problem. | Obstruction occurred twice in vessel A in 80 shots. | Although bulk densities were within the target value of 10 to 14 g/L, when second-stage expanded particles in vessel A were tried to be discharged after bulk densities were measured, second-stage expanded particles remained in conical portion of vessel A and it took time for cleaning. |

|  |  | Example | | | Comparative Example |
|---|---|---|---|---|---|
|  |  | 6 | 7 | 8 | 1 |
| Angle α of conical portion | ° | 60 | 50 | 60 | 90 |
| Internal pressure of vessel A immediately before filling into vessel B | Pa | $30 \times 10^3$ | $30 \times 10^3$ | $30 \times 10^3$ | Atmospheric pressure |
| Internal pressure of vessel B immediately before filling into vessel B | Pa | $30 \times 10^3$ | $30 \times 10^3$ | $20 \times 10^3$ | Atmospheric pressure |
| Conditions of second-stage expanded particles |  | Obstruction occurred twice in vessel A in 80 shots. | Obstruction occurred four times in vessel A in 80 shots. | Although bulk densities were within the target value of 10 to 14 g/L, bulk densities entirely higher than those in Example 1 were obtained. | Bulk densities were largely varied among shots and original bulk densities could not be measured. Bulk densities of second-stage expanded particles that had been recovered from contraction by heating processing were also varied largely. |

Example 2

In the <Bulk Density Measurement for Second-stage Expanded Particles>, the second-stage expansion was performed by operations same as those in Example 1 except that the bulk density was measured in the following manner using the bulk-density measuring device as illustrated in FIG. 2, and evaluation was performed. An evaluation result is illustrated in Table 2.

(1) The contracted second-stage expanded particles were input in a state where the vessel A input valve 2 was closed until the input hopper 1 (volume 3 L) was substantially filled with them.

Subsequently, in a state where the vessel A input valve 2 (inner diameter 50 mm) was opened and the vessel A discharge valve 3 was closed, the second-stage expanded particles were put in vessel A (volume 4 L, angle of the conical portion α=90°) and the vessel A input valve 2 was closed.

(2) Thereafter, the closed states of the vessel B discharge valve 4 and the valve 10 were checked. After that, the valve 11 (automatic valve) provided on the pipe connecting the three-way valve 7 and vessel A and the valve 12 (automatic valve) provided on the pipe connecting the three-way valve 7 and vessel B were opened and the pressure-reducing unit 8 (vacuum pump) was driven so as to reduce the internal pressures of vessel A and vessel B through the three-way valve 7 (to 20×10³ Pa for the internal pressure of vessel A, to 30×10³ Pa for the internal pressure of vessel B). In this case, the automatic valves 11 and 12 were set to be closed at a time point at which vessel A and vessel B reached the internal pressures as indicated in Table 2. With this, the second-stage expanded particles in vessel A were swollen and recovered from contraction.

(3) The vessel A discharge valve 3 (inner diameter 50 mm) was opened, and the second-stage expanded particles that were swollen in vessel A were transported and filled into vessel B having a volume V=1 L in a freely falling manner. Then, the vessel A discharge valve 3 was closed.

(4) Thereafter, the vessel B discharge valve 4 (inner diameter 50 mm) was opened and total amount of the second-stage expanded particles was discharged to the discharge receiving tray 5. Then, the weight [W(g)] of the discharged particles was measured using the scale 6 so as to calculate the bulk density [W/V(g/L)]. When the second-stage expanded particles were discharged to the discharge receiving tray 5, the valve 10 was opened and the air was ejected into vessel B from the outside through the forcible discharge unit 9 (pipe) so as to prevent the second-stage expanded particles from remaining in vessel B.

(5) After the bulk density was measured, the valve 2, the valve 3, and the valve 4 were opened and the second-stage expanded particles remaining in the input hopper 1 and vessel A were discharged.

When the second-stage expansion for 80 shots was executed as described above, the bulk densities from the first shot to the eightieth shot were within the target value of 10 to 14 g/L and stable. In addition, no problem such as obstruction with the second-stage expanded particles in the device occurred at all.

Example 3

The second-stage expansion was performed by operations same as those in Example 2 except that the bulk-density measuring device having an angle α of the conical portion of vessel A, which was set to 60°, was used, and evaluation was performed. An evaluation result is illustrated in Table 2.

When the second-stage expansion for 80 shots was executed, the bulk densities from the first shot to the eightieth shot were within the target value of 10 to 14 g/L and stable. In addition, no problem such as obstruction with the second-stage expanded particles in the device occurred.

Example 4

The second-stage expansion was performed by operations same as those in Example 2 except that the bulk-density measuring device having an angle α of the conical portion of vessel A, which was set to 500, was used, and evaluation was performed. An evaluation result is illustrated in Table 2.

When the second-stage expansion for 80 shots was executed, the bulk densities from the first shot to the eightieth shot were within the target value of 10 to 14 g/L and stable. However, obstruction with the second-stage expanded particles occurred twice in vessel A. Every time the obstruction occurred, the bulk density measurement was interrupted to dissolve the obstruction with the second-stage expanded particles in vessel A. Then, the measurement was restarted.

Example 5

The second-stage expansion was performed by operations same as those in Example 2 except that the bulk-density measuring device having an angle α of the conical portion of vessel A, which was set to 130°, was used, and evaluation was performed. An evaluation result is illustrated in Table 2.

When the second-stage expansion for 80 shots was executed, the bulk densities from the first shot to the eightieth shot were within the target value of 10 to 14 g/L and stable. However, when the second-stage expanded particles in vessel A were tried to be discharged and cleaned after the bulk density was measured, the second-stage expanded particles remained in the conical portion of vessel A and it took time for the cleaning.

Example 6

The second-stage expansion was performed by operations same as those in Example 1 except that the bulk-density measuring device having an angle α of the conical portion of vessel A, which was set to 60°, was used and the internal pressures of vessel A and vessel B were set to the internal pressures as illustrated in Table 2 (in pressure-equalized states of $30 \times 10^3$ Pa for vessel A and vessel B), and evaluation was performed. An evaluation result is illustrated in Table 2.

When the second-stage expansion for 80 shots was executed, the bulk densities from the first shot to the eightieth shot were within the target value of 10 to 14 g/L and stable. However, obstruction with the second-stage expanded particles occurred twice in vessel A. Every time the obstruction occurred, the bulk density measurement was interrupted to dissolve the obstruction with the second-stage expanded particles in vessel A. Then, the measurement was restarted.

Example 7

The second-stage expansion was performed by operations same as those in Example 1 except that the bulk-density measuring device having an angle α of the conical portion of vessel A, which was set to 50°, was used and the internal pressures of vessel A and vessel B were set to the internal pressures as illustrated in Table 2 (in pressure-equalized states of $30 \times 10^3$ Pa for vessel A and vessel B), and evaluation was performed. An evaluation result is illustrated in Table 2.

When the second-stage expansion for 80 shots was executed, the bulk densities from the first shot to the eightieth shot were within the target value of 10 to 14 g/L and stable. However, obstruction with the second-stage expanded particles occurred four times in vessel A. Every time the obstruction occurred, the bulk density measurement was interrupted to dissolve the obstruction with the second-stage expanded particles in vessel A. Then, the measurement was restarted.

Example 8

The second-stage expansion was performed by operations same as those in Example 2 except that the bulk-density measuring device having an angle α of the conical portion of vessel A, which was set to 60°, was used and the internal pressures of vessel A and vessel B were set to the internal pressures as illustrated in Table 2 ($30 \times 10^3$ Pa for the internal pressure of vessel A and $20 \times 10^3$ Pa for the internal pressure of vessel B), and evaluation was performed. An evaluation result is illustrated in Table 2.

When the second-stage expansion for 80 shots was executed, the bulk densities from the first shot to the eightieth shot were within the target value of 10 to 14 g/L and stable. However, the bulk densities entirely higher than those in Example 1 were obtained. It is considered that a part of the second-stage expanded particles were forcibly filled into vessel B from vessel A without being filled in the freely falling manner and vessel B was filled with the second-stage expanded particles in a slightly congested manner. It should be noted that no problem such as obstruction with the second-stage expanded particles in the device occurred.

Although the disclosure has been described with respect to only a limited number of embodiments, those skilled in the art, having benefit of this disclosure, will appreciate that various other embodiments may be devised without departing from the scope of the present invention. Accordingly, the scope of the present invention should be limited only by the attached claims.

REFERENCE SIGNS LIST

A Vessel A
B Vessel B
1 Input hopper
2 Input valve
3 Vessel A discharge valve
4 Vessel B discharge valve
5 Discharge receiving tray
6 Scale
7 Three-way valve
8 Pressure-reducing unit (vacuum pump)
9 Forcible discharge unit (pipe)
10 Valve provided in forcible discharge unit
11 Valve provided on pipe between three-way valve 7 and vessel A
12 Valve provided on pipe between three-way valve 7 and vessel B

The invention claimed is:

1. A bulk-density measuring device comprising:
a first vessel in which contracted pre-expanded particles are swollen and recovered from contraction in a pressure-reduced state where a vessel's internal pressure is lower than atmospheric pressure;
a second vessel in which the pre-expanded particles after being swollen in the first vessel are filled in a pressure-reduced state where a vessel's internal pressure is lower than atmospheric pressure, and into which the swollen pre-expanded particles of a constant volume are collected fractionally;
a pressure-reducing unit that adjusts the vessels internal pressures of the first vessel and the second vessel to be lower than the atmospheric pressure; and
a scale that measures a weight of the swollen pre-expanded particles filled in the second vessel.

2. The bulk-density measuring device according to claim 1, further comprising, between the first vessel and the second vessel, a first vessel discharge valve that discharges the swollen pre-expanded particles accommodated in the first vessel in a freely falling manner and fills the second vessel with the swollen pre-expanded particles.

3. The bulk-density measuring device according to claim 1, further comprising a second vessel discharge valve that discharges the swollen pre-expanded particles filled in the second vessel to the scale.

4. The bulk-density measuring device according to claim 1, further including a first valve and a second valve which are capable of making the internal pressures of the first vessel and the second vessel different from each other.

5. The bulk-density measuring device according to claim 1, wherein the vessel has a conical portion and an angle α of the conical portion is equal to or larger than 60° and equal to or smaller than 120°.

6. The bulk-density measuring device according to claim 1, wherein at least one valve for controlling the vessel's internal pressure is arranged on a pipe connecting the first vessel and the pressure-reducing unit and/or a pipe connecting the second vessel and the pressure-reducing unit.

7. The bulk-density measuring device according to claim 1, wherein the second vessel comprises a forcible discharge unit that forcibly discharges the swollen pre-expanded particles filled in the second vessel.

8. The bulk-density measuring device according to claim 1, wherein the first vessel comprises a level switch that controls an accommodation amount of the pre-expanded particles to be accommodated.

9. A method for measuring bulk density of pre-expanded particles, the method comprising:
a) collecting a part or all of the contracted pre-expanded particles and transporting the contracted pre-expanded particles to a first vessel;
b) swelling the contracted pre-expanded particles to recover from contraction by making an internal pressure of the first vessel in a pressure-reduced state lower than atmospheric pressure;
c) making an internal pressure of a second vessel in a pressure-reduced state lower than atmospheric pressure;
d) filling the second vessel with the pre-expanded particles after being swollen in the first vessel in the pressure-reduced state where the vessel's internal pressure is lower than the atmospheric pressure by opening a valve between the first vessel and the second vessel and fractionally collecting the swollen pre-expanded particles of a constant volume; and
e) measuring a weight of the swollen pre-expanded particles by a scale after the internal pressure of the second vessel is returned to the atmospheric pressure and the swollen pre-expanded particles filled in the second vessel are discharged.

10. The method for measuring the bulk density of the pre-expanded particles according to claim 9, wherein in step c), the internal pressure of the second vessel is set to be higher than the internal pressure of the first vessel.

11. The method for measuring the bulk density of the pre-expanded particles according to claim 9, wherein in step c), the internal pressure of the second vessel is set to be lower than the internal pressure of the first vessel.

12. The method for measuring the bulk density of the pre-expanded particles according to claim 9, wherein in step c), the internal pressures of the first vessel and the second vessel are set to be equivalent.

13. The method for measuring the bulk density of the pre-expanded particles according to claim 9, wherein the internal pressures of the first vessel and the second vessel are equal to or higher than $10 \times 10^3$ Pa and equal to or lower than $90 \times 10^3$ Pa.

14. The method for measuring the bulk density of the pre-expanded particles according to claim 9, wherein in step a), a bulk volume of the contracted pre-expanded particles transported to the first vessel is equal to or higher than 20% and equal to or lower than 80% of an internal volume of the first vessel.

15. The method for measuring the bulk density of the pre-expanded particles according to claim 9, wherein
in step d), the filling of the second vessel with the swollen pre-expanded particles is performed in a freely falling manner, and
in step e), the discharging of the swollen pre-expanded particles from the second vessel is performed at least using a forcible discharge unit.

16. The method for measuring the bulk density of the pre-expanded particles according to claim 9, wherein the pre-expanded particles are polyolefin resin pre-expanded particles.

17. A method for manufacturing pre-expanded particles, the method comprising:
adjusting expanding conditions of the pre-expanded particles in a pre-expanding device by comparing a measurement result and target bulk density; and
feeding back a result of the comparison to the pre-expanding device after bulk density of the pre-expanded particles is measured by the measuring method according to claim 9.

18. The method for manufacturing the pre-expanded particles according to claim 17, wherein the pre-expanding device is a second-stage expanding machine.

19. The method for manufacturing the pre-expanded particles according to claim 17, wherein the pre-expanded particles are polyolefin resin pre-expanded particles having bulk density of equal to or higher than 8 g/L and lower than 30 g/L.

* * * * *